United States Patent
Amanullah et al.

(10) Patent No.: US 8,401,272 B2
(45) Date of Patent: Mar. 19, 2013

(54) PATTERNED WAFER DEFECT INSPECTION SYSTEM AND METHOD

(75) Inventors: Ajharali Amanullah, Singapore (SG); Lin Jing, Singapore (SG); Chunlin Luke Zeng, Singapore (SG)

(73) Assignee: ASTI Holdings Limited, Singapore (SG)

( * ) Notice: Subject to any disclaimer, the term of this patent is extended or adjusted under 35 U.S.C. 154(b) by 1317 days.

(21) Appl. No.: 11/888,827

(22) Filed: Aug. 2, 2007

(65) Prior Publication Data
US 2009/0034831 A1    Feb. 5, 2009

(51) Int. Cl.
*G06K 9/00* (2006.01)
(52) U.S. Cl. ......................................................... 382/145
(58) Field of Classification Search .................. 382/141, 382/145, 152, 209, 228; 29/833; 438/16
See application file for complete search history.

(56) References Cited

U.S. PATENT DOCUMENTS

| | | | |
|---|---|---|---|
| 5,640,200 A | 6/1997 | Michael | |
| 5,850,466 A | 12/1998 | Schott | |
| 6,319,732 B1 * | 11/2001 | Dils et al. ........................... | 438/7 |
| 6,330,354 B1 | 12/2001 | Companion et al. | |
| 6,797,954 B2 | 9/2004 | Shinada et al. | |
| 6,920,241 B1 | 7/2005 | Dutta-Choudhury et al. | |
| 6,979,823 B2 | 12/2005 | Shinada et al. | |
| 2002/0076096 A1 * | 6/2002 | Silber et al. .................... | 382/152 |
| 2004/0092047 A1 * | 5/2004 | Lymberopoulos et al. ..... | 438/17 |
| 2004/0179715 A1 * | 9/2004 | Nilsson et al. ................. | 382/103 |
| 2005/0281452 A1 * | 12/2005 | Usikov ........................... | 382/141 |

OTHER PUBLICATIONS

From Corresponding PCT patent application (PCT/SG2008/000286): International Search Report mailed Jan. 30, 2009 (2 pgs.); International Preliminary Report on Patentability mailed Feb. 2, 2010 (1 pg.); and Written Opinion of the International Searching Authority mailed Jan. 30, 2009 (4 pgs.).

* cited by examiner

*Primary Examiner* — Edward Park
(74) *Attorney, Agent, or Firm* — Jackson Walker L.L.P.; Christopher J. Rourk

(57) ABSTRACT

A system for inspecting semiconductor devices is provided. The system includes a region system selecting a plurality of regions from a semiconductor wafer. A golden template system generates a region golden template for each region, such as to allow a die image to be compared to golden templates from a plurality of regions. A group golden template system generates a plurality of group golden templates from the region golden templates, such as to allow the die image to be compared to golden templates from a plurality of group golden templates.

21 Claims, 3 Drawing Sheets

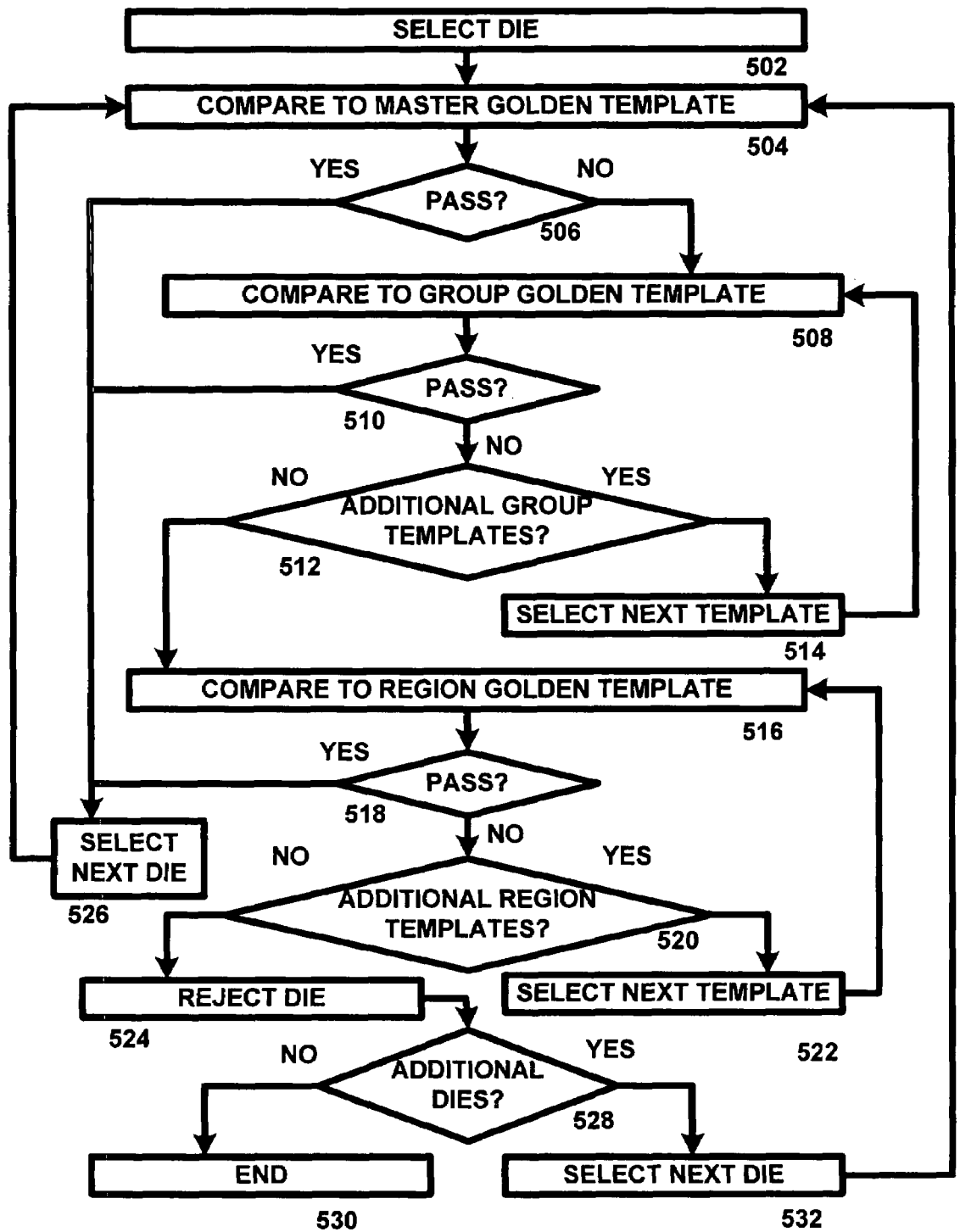
FIG. 5

# PATTERNED WAFER DEFECT INSPECTION SYSTEM AND METHOD

FIELD OF THE INVENTION

The invention relates to wafer inspection, and in particular to a system and method for utilizing multiple golden templates to reduce false rejections of dies.

BACKGROUND OF THE INVENTION

It is known to use a golden template to inspect dies from semiconductor wafers. Such golden templates are die images that are benchmarks, such that when they are compared with a die image under inspection, the die image under inspection can be judged based on the degree of similarity or difference to the golden template.

While golden template inspection is useful, the best golden template inspection techniques result in a large number of false rejections. Whenever a die is improperly rejected, it must either be manually inspected by an operator, which requires costly manual inspection, or rejected, which negatively impacts the yield of dies from the wafer.

SUMMARY OF THE INVENTION

In accordance with the present invention, a system and method for performing golden template inspection are provided that overcome known problems with systems and methods for performing golden template inspection.

In particular, a system and method for performing golden template inspection are provided which utilize a hierarchy of golden templates that can be used to test rejected dies, so as to reduce the number of false rejections.

In accordance with an exemplary embodiment of the present invention, a system for inspecting semiconductor devices is provided. The system includes a region system selecting a plurality of regions from a semiconductor wafer. A golden template system generates a region golden template for each region, such as to allow a die image to be compared to golden templates from a plurality of regions. A group golden template system generates a plurality of group golden templates from the region golden templates, such as to allow the die image to be compared to golden templates from a plurality of group golden templates.

The present invention provides many important technical advantages. One important technical advantage of the present invention is an inspection system that utilizes an hierarchy of golden templates that allow acceptable dies that have been rejected due to otherwise insubstantial regional variations in certain image characteristics to be detected without manual intervention.

Those skilled in the art will further appreciate the advantages and superior features of the invention together with other important aspects thereof on reading the detailed description that follows in conjunction with the drawings.

BRIEF DESCRIPTION OF THE SEVERAL VIEWS OF THE DRAWINGS

FIG. 5 is flow chart of a method for testing die images using an hierarchy of golden template data in accordance with an exemplary embodiment of the present invention.

DETAILED DESCRIPTION OF PREFERRED EMBODIMENTS

Figure 1:
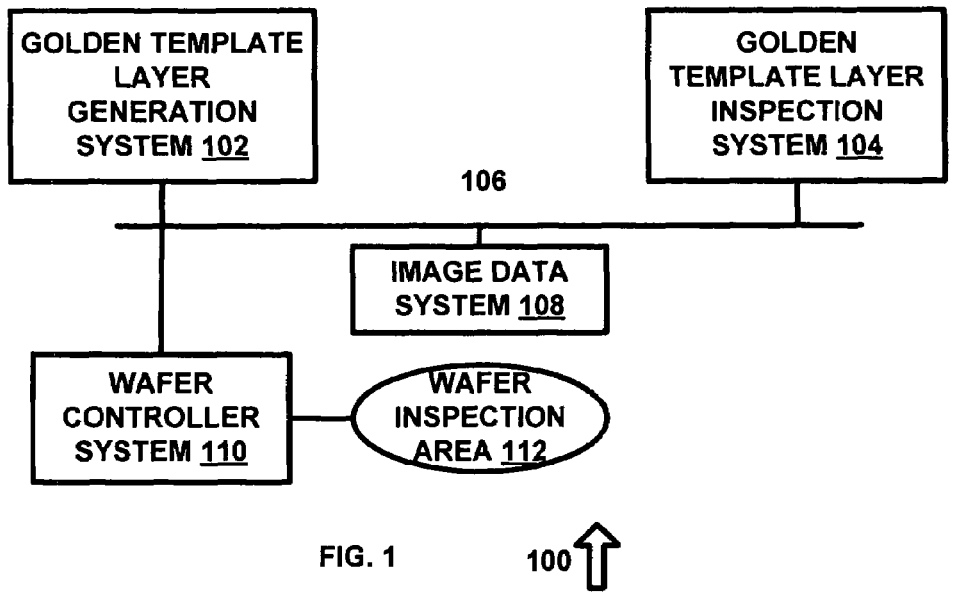
FIG. 1 is a diagram of a system for performing a golden template inspection in accordance with an exemplary embodiment of the present invention.

In the description that follows, like parts are marked throughout the specification and drawings with the same reference numerals, respectively. The drawing figures might not be to scale, and certain components can be shown in generalized or schematic form and identified by commercial designations in the interest of clarity and conciseness.

FIG. 1 is a diagram of a system 100 for performing a golden template inspection in accordance with an exemplary embodiment of the present invention. System 100 allows multiple golden templates to be used to inspect semiconductor dies so as to reduce the number of false rejections.

System 100 includes golden template layer generation system 102 and golden template layer inspection system 104, each of which can be implemented in hardware, software, or a suitable combination of hardware and software and which can be one or more software systems operating on a general purpose processing computer. As used herein, a hardware system can include a combination of discrete components, an integrated circuit, an application-specific integrated circuit, a field programmable gate array, or other suitable hardware. A software system can include one or more objects, agents, threads, lines of code, subroutines, separate software applications, two or more lines of code or other suitable software structures operating in two or more software applications or on two or more processors, or other suitable software structures. In one exemplary embodiment, a software system can include one or more lines of code or other suitable software structures operating in a general purpose software application, such as an operating system, and one or more lines of code or other suitable software structures operating in a specific purpose software application.

Golden template layer generation system 102 and golden template layer inspection system 104 are coupled to communications medium 106. As used herein, the term "coupled" and its cognate terms such as "couples" or "couple," can include a physical connection (such as a wire, optical fiber, or a telecommunications medium), a virtual connection (such as through randomly assigned memory locations of a data memory device or a hypertext transfer protocol (HTTP) link), a logical connection (such as through one or more semiconductor devices in an integrated circuit), or other suitable connections. In one exemplary embodiment, communications medium 106 can be a network or other suitable communications media.

Image data system 108 is coupled to communications medium 106, and generates image data for a wafer in wafer inspection area 112. The wafer may be subdivided into predetermined rectangular dies, and image data system 108 allows images to be obtained of each die, such as by indexing, locating dies within the wafer, or in other suitable manners. Wafer controller system 110 is coupled to communications medium 106 and wafer inspection area 112. In this exemplary embodiment, wafer controller system 110 allows wafers to be moved so as to allow image data system 108 to generate image data of different sections of the wafer, different wafers, or for other suitable purposes.

In operation, system 100 allows wafers to be inspected utilizing multiple golden templates. In one exemplary embodiment, golden template layer generation system 102 generates two or more golden templates for use in inspecting wafers. In this exemplary embodiment, golden templates can be generated from different regions of the wafer, from combinations of regional golden templates, or in other suitable manners so as to have a number of golden templates with which to test and inspect wafers with.

Golden template layer inspection system 104 receives the golden templates generated by golden template layer generation system 102 and performs the inspection of one or more dies from a wafer in wafer inspection area 112. In one exemplary embodiment, image data system 108 can generate image data for a die on a wafer in wafer inspection area 112, and that image data can be compared to a first golden template by golden template layer inspection system 104. If the die passes inspection, image data system 108 retrieves another die image for inspection. Otherwise, golden template layer inspection system 104 can select another golden template for use in the inspection process. In one exemplary embodiment, there can be a master golden template and layers of groups of golden templates formed from regions and combinations of regions, such that if the master golden template inspection of a die image fails, additional inspections can be made so as to eliminate false rejections. In this manner, if a die image initially fails inspection utilizing the master golden template, it can be determined whether the die image is acceptable based on one or more golden templates from regions or composites of regions so as to avoid false rejects of acceptable dies.

Figure 2:
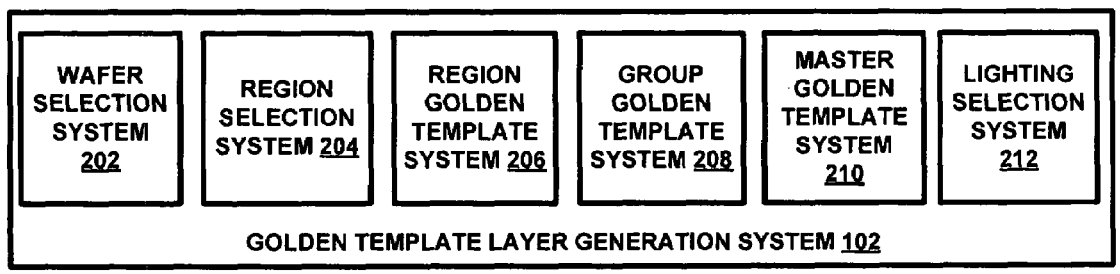
FIG. 2 is a diagram of a system for golden template layer generation in accordance with an exemplary embodiment of the present invention.

FIG. 2 is a diagram of a system 200 for golden template layer generation in accordance with an exemplary embodiment of the present invention. System 200 includes golden template layer generation system 102 and wafer selection system 202, region selection system 204, region golden template system 206, group golden template system 208, master golden template system 210, and lighting selection system 212, each of which can be implemented in hardware, software, or a suitable combination of hardware and software, and which can be one or more software systems operating on a general purpose processing platform.

Wafer selection system 202 allows one or more wafers to be selected for generation of golden template images. In one exemplary embodiment, wafer selection system 202 can select one of a plurality of wafers for generation of golden templates, can select two or more of a plurality of wafers for generation of golden templates, can combine golden templates from wafers, or can perform other suitable processes. In another exemplary embodiment, wafers can be selected for generation of golden template images based on illumination of different features using different types of illumination. For example, under direct lighting, certain features may be observable that are not observable under lighting that illuminates the surface at an angle of incidence or a range, such as from 5 to 30 degrees off the direct axis, 60 to 90 degrees off the direct axis, using different colors of light, or other suitable ranges of lighting angle incidence. In this exemplary embodiment, different sets of golden templates can be generated for each different type of illumination, and the features that are illuminated by each type of illumination can be used to select the golden templates for each region. As such, the identification of one or more features and the comparison of different die images relative to those features can be used to select the golden template for a given region.

Region selection system 204 allows one or more regions on a wafer to be identified from which a golden template for that region is to be generated. In one exemplary embodiment, region selection system 204 can evaluate variations in brightness, differences in locations of features, histogram data or other suitable data to identify regions. Likewise, region selection system 204 can have predetermined regions from which golden templates are to be extracted.

Region golden template system 206 generates a golden template from a region. In one exemplary embodiment, image data for a plurality of dies from a region is generated by region golden template system 206 based on an identified region from region selection system 204. Region golden template system 206 then selects one of the dies within the region to be the region golden template, generates a region golden template from a composite of the die images, or utilizes other suitable processes for generating a region golden template. In another exemplary embodiment, a golden template can be selected based on the location of identified or predetermined features, pixel brightness variations, histogram data, data from predetermined regions of the die image, or in other suitable manners.

Group golden template system 208 receives region golden template data and generates group golden template data. In one exemplary embodiment, group golden template system 208 can receive a plurality of region golden templates from region golden template system 206, and can create group golden templates by combining two or more region golden templates in a suitable manner, such as by averaging pixel values in predetermined areas, by selecting predetermined sections of each die based on an analysis of pixel brightness variation or histogram data, by selecting one of the region golden templates based on a comparison with one or more of the other region golden templates from a single wafer or multiple wafers, or in other suitable manners.

Master golden template system 210 receives the group golden templates from group golden template system 208 and generates a single master golden template or a suitable number of master golden templates. In one exemplary embodiment, master golden template system 210 can utilize group golden templates and region golden templates from a plurality of wafers so as to generate master golden templates from each wafer, for each of a plurality of wafers, or other suitable combinations, such as by averaging pixel values in predetermined areas, by selecting predetermined sections of each die based on an analysis of pixel brightness variation or histogram data, by selecting one of the group golden templates based on a comparison with one or more of the other group golden templates from a single wafer or multiple wafers, or in other suitable manners. In addition, a fourth, fifth, or other suitable number of levels of golden template groups can also or alternatively be used, such as by forming group golden templates from sub-groups (e.g., from wafers in regions around the periphery of the die and wafers in regions internal to the die), or in other suitable manners.

Lighting selection system 212 allows golden template images to be selected based on two or more different types of lighting, such as lighting angle, lighting intensity, lighting color, or other suitable lighting variations. In one exemplary embodiment, each set of region golden templates, group golden templates, and the master golden template can be selected under different lighting conditions, so as to form a first set of region golden templates, group golden templates, and master golden template for a first lighting condition, such as using a light source that illuminates the wafers parallel to the optical axis, a second set of region golden templates, group golden templates, and master golden template for a second lighting condition, such as using a light source that illuminates the wafers at 60 to 90 degrees from the optical axis, a third set of region golden templates, group golden templates, and master golden template for a third lighting condition, such as using a light source that illuminates the wafers at 5 to 30 degrees from the optical axis, or other suitable lighting sources. Such different lighting sources can be used to illuminate different physical features, such that the geometric difference between the specific features being illuminated varies as a function of lighting source.

In operation, system 200 allows golden templates to be generated for a layered golden template inspection system. In one exemplary embodiment, system 200 allows golden templates from different wafers, from different regions of dies, from groups of regions of dies, or from groups of dies to be used so as to increase the number of golden templates that can be used to perform an inspection, so as to reduce the number of false rejections of acceptable dies.

Figure 3:
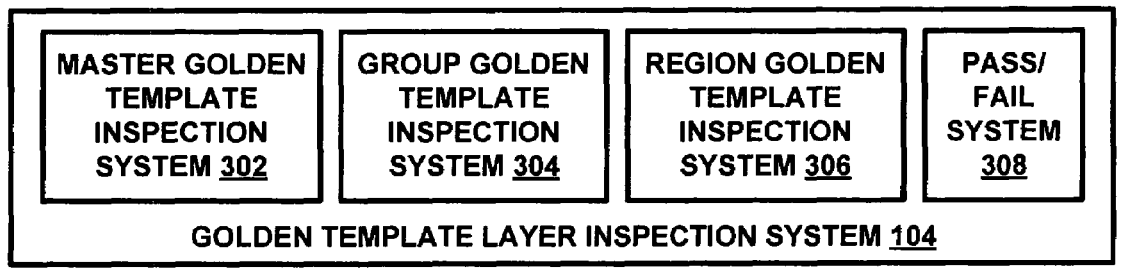
FIG. 3 is a diagram of a system for golden template layer inspection in accordance with an exemplary embodiment of the present invention.

FIG. 3 is a diagram of a system 300 for golden template layer inspection in accordance with an exemplary embodiment of the present invention. System 300 includes golden template layer inspection system 104 and master golden template inspection system 302, group golden template inspection system 304, region golden template inspection system 306, and pass fail system 308, each of which can be implemented in hardware, software or a suitable combination of hardware and software, and which can be one or more software systems operating on a general purpose processing platform.

Master golden template inspection system 302 receives die image data and performs a master golden template inspection. In one exemplary embodiment, the die image data can be compared to the master golden template in order to identify pass/fail criteria, such as variations in brightness of pixels in predetermined areas, variations in histogram data for pixels, or other suitable die inspection data. Likewise, intermediate pass/fail data can be generated, such as for certain areas, or setting acceptance or rejection of the die based upon results of additional golden template tests.

Group golden template inspection system 304 can perform group golden template inspection on one or more die images that are being inspected. In one exemplary embodiment, a die image can be compared to a first group golden template to determine whether it has passed or failed. If the inspection for the first group golden template results in failure or an intermediate condition, one or more addition group golden templates can then be selected for use in inspecting the die image data. Likewise, intermediate pass/fail data can be generated, such as for certain areas, or setting acceptance or rejection of the die based upon results of additional golden template tests.

Region golden template inspection system 306 performs golden template inspection of die image data using region golden templates. In one exemplary embodiment, if a die image data set has failed inspection from a group golden template inspection process, a master golden template inspection process, or other suitable golden template inspection processes, region golden template inspection system 306 can compare the die image data to one or more region golden templates. In one exemplary embodiment if comparison of a first region golden template to the die image data results in a fail indication or intermediate indication, additional region golden templates can be used to test the die image. Likewise, intermediate pass/fail data can be generated, such as for certain areas, or setting acceptance or rejection of the die based upon results of additional golden template tests.

Pass fail system 308 receives pass/fail data from the master golden template inspection system 302, group golden template inspection system 304, and region golden template inspection system 306 and coordinates the processing of die image data for inspection. In one exemplary embodiment, when master golden template inspection system 302 generates a fail indication, pass fail system 308 will transfer image data for a die image to group golden template inspection system 304. In this manner, additional die image data can be inspected by master golden template inspection system 302 while group or region golden template inspection processes are being performed.

Likewise, pass fail system 308 can generate an indication to remove a rejected die, can call operator attention to a die for additional manual inspection, or can perform other suitable processes.

In operation, system 300 provides an inspection system that utilizes multiple golden templates so as to reduce the number false rejects of acceptable dies.

Figure 4:
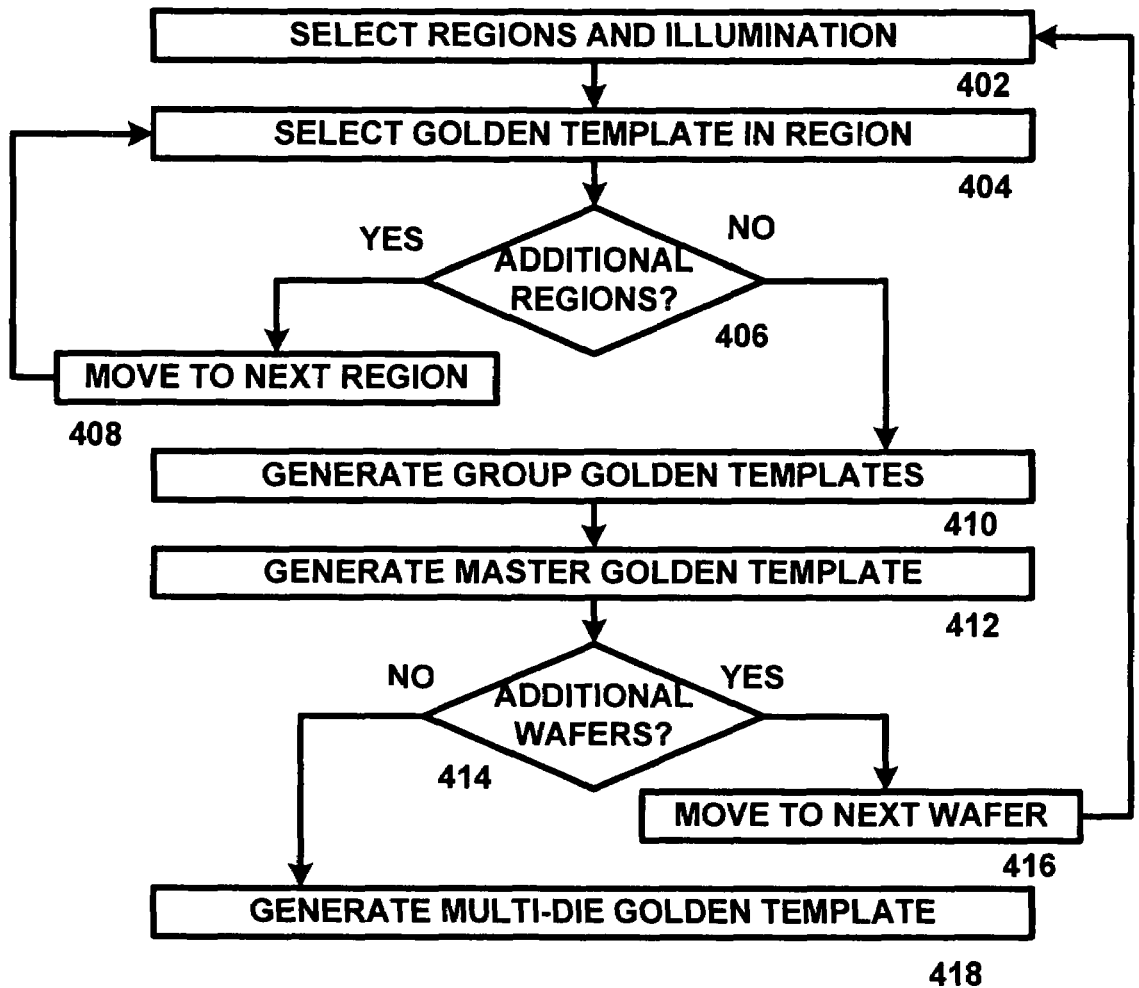
FIG. 4 is a diagram of a method for generation of layers of golden template data in accordance with an exemplary embodiment of the present invention.

FIG. 4 is a diagram of a method 400 for generation of layers of golden template data in accordance with an exemplary embodiment of the present invention. Method 400 begins at 402 where one or more regions and an illumination source are selected for a die. In one exemplary embodiment, the number of regions can be selected based upon predetermined areas of the die, based upon image data analysis of image data from the die, based on historical data for areas in which region golden templates should be selected, or other suitable data. The illumination source can be selected from one of two or more different illumination sources that are used to illuminate different surface features of each die, such as by using different angle of incidence, colors, or other suitable variations in illumination. The dimensional relationship of such features can then be used to select the golden template within a region. The method then proceeds to 404.

At 404 golden templates from two or more regions are selected. In one exemplary embodiment, region golden templates can be selected by analyzing individual die images in a region and identifying a die image or a composite die image that can be used to inspect other die images from other wafers so as to result in a pass fail indication as to whether the individual die is acceptable or contains defects that render it unacceptable. In one exemplary embodiment, one or more features that are prominent under a angle or illumination can be used to select the golden templates, such as by selecting golden templates based on the dimensional relationship between such features. The method then proceeds to 406.

At 406, it is determined whether additional regions need to be analyzed to select golden templates in those regions. If it is determined at 406 that there are additional regions, the method proceeds to 408 where die image data is obtained from the next region. In one exemplary embodiment, image data can be generated for an entire wafer, can be generated by moving the wafer relative to the image data generation system, can be generated by moving the image data generation system relative to the wafer, or in other suitable matters. The method then returns to 404. Otherwise, if it is determined that there are no more additional regions at 406, the method proceeds to 410.

At 410, the group golden templates are generated. In one exemplary embodiment, group golden templates can be generated using one or more combinations, such as by comparing the region golden templates to select two or more region golden templates that are best representative of the group, by combining each region golden template with another region golden template, by combining each region golden template with two or more other region golden templates, by combining predetermined region golden templates with other region golden templates, by combining sections of region golden templates with different sections of other region golden templates, by combining region golden templates based upon pixel, histogram, or other suitable data, or by combining region golden templates in other suitable manners. Likewise, two or more sets of group golden templates can also or alternatively be generated, such as by combining region golden templates from similar regions (such as from the periphery of the wafer versus the center of the wafer), based on historical data, the location of features in the golden template images, or in other suitable manners. The method then proceeds to 412.

At 412, a master golden template is generated. In one exemplary embodiment, the master golden template can be generated utilizing the region golden templates, the group golden templates, or both the region and group golden templates in the manner previously described for generation of group golden templates from region golden templates, or in other suitable manners. The method then proceeds to 414.

At 414, it is determined whether there are additional wafers to be processed. For example, golden templates can be generated based on data from multiple wafers using multiple dies. If it is determined at 414 if there are additional wafers, the method proceeds to 416 where the next wafer is selected. In one exemplary embodiment, a wafer can be selected by moving a wafer from a wafer storage area via conveyor, by use of a pick and place tool, or in other suitable manners. The method then returns 402.

If it is determined at 414 that there are no additional wafers, then the method proceeds to 418 where a multiple die golden template is generated. In one exemplary embodiment, where multiple wafers have been used, a multiple wafer golden template is generated. In addition, a golden template group is generated for use in a layered golden template inspection process.

In operation, method 400 allows a related group of golden templates to be created that allows die image data to be analyzed so as to reduce the number of false rejects. In this manner, acceptable die images can be detected using a prioritized hierarchy of golden templates that allow dies that fail initial golden template testing to be tested against additional groups or region golden templates so as to decrease the number of false rejects.

FIG. 5 is flow chart of a method 500 for testing die images using an hierarchy of golden template data in accordance with an exemplary embodiment of the present invention. Method 500 begins at 502 where a die is selected. In one exemplary embodiment, the die can be selected from a set of image data generated by an image data system that moves across a wafer that is being inspected, from a set of image data that is generated of an entire wafer under inspection, or in other suitable manners. Then proceed to 504.

At 504, the die image data is compared to a master golden template. In one exemplary embodiment, the comparison can include comparison of predetermined areas, features, histogram data, or other suitable comparison data. Then proceeds to 506.

At 506, it is determined whether the result is a pass or fail. In one exemplary embodiment, there may also be intermediate stages that result in subsequent testing against subsequent golden templates from groups or regions. If it is determined at 506 that the die has passed golden template testing, the method proceeds to 526 and the next die is selected. The method then returns to 504. Likewise, if it is determined at 506 that the die image has not passed the master golden template test the method proceeds to 508.

At 508 the die image data is compared to group golden template data. In one exemplary embodiment, the group golden template data can be selected from a set of groups that are used to select the golden template, can be selected from groups from multiple wafers, or other suitable groups. The method then proceeds to 510 where it is determined whether the results indicate a pass or fail. As previously indicated, a pass indication can be dependent on previous intermediate results at 506 and a subsequent acceptable result at 510. Likewise, other suitable pass/fail criteria can be utilized. If it is determined that 510 the die image data has passed inspection testing, the method proceeds to 526 and the next die image is selected. Otherwise the method proceeds to 512 where it is determined whether there are additional group templates available for inspecting the die image data. If it is determined that there are additional group templates the methods proceeds to 514 where the next group template is selected. The method then returns to 508. Otherwise the method proceeds to 516 where the die image data is compared to region golden templates. In one exemplary embodiment, the region golden template data can be selected based on probabilistic data, a hierarchy of region golden templates that most effective, based on the region of the wafer from which the die image has been gathered, or other suitable processes can be used. The method then proceeds to 518.

At 518 it is determined whether the die has passed the region golden wafer test. It is determined at 518 that the die has passed, the method proceeds to 526. As previously discussed, a pass result can also be generated based on intermediate test results from master or group golden template testing. If it is determined at 518 that the test has failed, the method proceeds to 520 where it is determined whether there are additional region golden templates available. If it is determined that there are additional region golden templates available, the method proceeds to 522 where the next region golden template is selected. The method then returns to 516.

Likewise, at 520 if it is determined that there are no additional regional golden templates the method proceeds to 524 where the die is rejected. The method then proceeds to 528 where it is determined whether there are additional dies. If additional dies are available for testing the method proceeds to 532 where the next die selected. The method then returns to 504. Otherwise the method proceeds to 530 and ends.

Likewise, one of ordinary skill in the art will understand that additional master golden templates, group templates and region templates from different wafers can also or alternatively be used in another selection step, such as by determining after the final region has been tested at 520 whether there are additional wafer golden template sets available for testing.

In operation, method 500 allows a die image to be analyzed based on a hierarchy of golden template data that reduces the frequency of false rejects so as to improve the efficiency of die inspection. Likewise, by using a hierarchy of golden templates, the inspection time for repeated golden template testing of die image data can be reduced. The hierarchy of die image data can be separated into different processors or different routines so as to allow multiple dies to be inspected.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A system for inspecting semiconductor devices comprising:
    a region system operating on a computer for selecting a plurality of regions from a semiconductor wafer carrying a plurality of semiconductor dies, each region comprising a plurality of semiconductor dies;

a region golden template system operating on the computer for generating a region golden template for each region within the plurality of regions, each region golden template defining a single benchmark image generated based upon a plurality of images corresponding to the plurality of semiconductor dies within a region;

a group golden template system for generating a plurality of group golden templates each group golden template defining a single benchmark image generated based upon at least one of the region golden templates;

a primary golden template system for generating a primary golden template from at least one of the group golden templates, the primary golden template defining a single benchmark image; and an inspection system for inspecting a semiconductor die, wherein the primary golden template is used to inspect the semiconductor die first, and the plurality of group golden templates are used to inspect the semiconductor die if the inspection with the primary golden template fails, and wherein the semiconductor die passes inspection if one or more inspection with the group golden template passes.

2. The system of claim 1 further comprising a group die inspection system for comparing a die image to one or more of the group golden templates if the die image fails inspection by a primary die inspection system, wherein each of the group golden templates correspond to a portion of the primary golden template.

3. The system of claim 2 further comprising a region die inspection system for comparing the die image to one or more of the region golden templates if the die image fails inspection by the group die inspection system after failing inspection by the primary die inspection system.

4. The system of claim 1 further comprising:
a primary die inspection system for comparing a die image to the primary golden template; and
an intermediate die inspection system for comparing the die image to one of the group golden templates.

5. The system of claim 4 further comprising a region die inspection system for comparing the die image to one of the region golden templates.

6. The system of claim 1 further comprising a lighting selection system for selecting one of two or more different lighting settings for illuminating the semiconductor wafer as a function of whether the region golden template or the group golden template is being generated.

7. The system of claims 1, further comprising a wafer controller system arranged to convey a plurality of distinct dies, so as to inspect each of the plurality of distinct dies.

8. The system of claim 1, wherein the region system is adapted to select at least two dies for generation of a plurality of region golden templates.

9. A method for inspecting semiconductor components comprising:
comparing a die image to a primary golden template using an inspection system, wherein the primary golden template represents a predetermined area of the die image, the primary golden template defining a single benchmark image;
comparing the die image to a group golden template using the inspection system if the die image fails the comparison to the primary golden template, wherein the group golden template represents a portion of the primary golden template, the group golden template defining a single benchmark image;
comparing the die image to a region golden template using the inspection system if the die image fails the comparison to the group golden template the region golden template defining a single benchmark image, the region golden template generated based upon a plurality of images corresponding to a plurality of semiconductor dies within a region of a semiconductor wafer, and wherein the semiconductor die passes inspection if one or more inspection with the group golden template passes.

10. The method of claim 9 wherein comparing the die image to the group golden template if the die image fails the comparison to the primary golden template comprises comparing the die image to each of two or more group golden templates if the die image fails the comparison to the primary golden template.

11. The method of claim 10 further comprising comparing the die image to each of two or more region golden templates if the die image fails the comparison to the group golden templates, wherein each region golden template represents a portion of one of the group golden templates and defining a single benchmark image.

12. The method of claim 9 further comprising selecting one of two or more different lighting settings.

13. The method of claim 9, further comprising conveying a plurality of distinct dies by a wafer controller system for inspecting each of the plurality of distinct dies.

14. A system for inspecting semiconductor devices comprising:
means for selecting a plurality of regions from a semiconductor wafer carrying a plurality of semiconductor dies, each region comprising a plurality of semiconductor dies;
means for generating a region golden template for each region corresponding to the plurality of regions, each region golden template defining a single benchmark image generated based upon a plurality of images corresponding to the plurality of semiconductor dies within a region; and
means for generating a plurality of group golden templates, each group golden template defining a single benchmark image generated based upon at least one of the region golden templates;
a primary golden template system for generating a primary golden template from at least one of the group golden templates, the primary golden template defining a single benchmark image; and
an inspection system for inspecting a semiconductor die, wherein the primary golden template is used to inspect the semiconductor die first, and the plurality of group golden templates are used to inspect the semiconductor die if the inspection with the primary golden template fails, and wherein the semiconductor die passes inspection if one or more inspection with the group golden template passes.

15. The system of claim 14 further comprising means for generating a primary golden template from a plurality of the group golden templates, the primary golden template defining a single benchmark image.

16. The system of claim 15 further comprising:
means for comparing a die image to the primary golden template;
means for comparing the die image to one of the group golden templates.

17. The system of claim 16 further comprising means for comparing the die image to one of the region golden templates.

18. The system of claim 14 further comprising means for comparing a die image to a primary golden template.

19. The system of claim 14 further comprising means for comparing a die image to a group golden template.

20. The system of claim 14 further comprising means for comparing a die image to a region golden template.

21. The system of claims 14, further comprising a means arranged to convey a plurality of distinct dies, so as to inspect each of the plurality of distinct dies.

* * * * *